United States Patent [19]
Goldstein et al.

[11] 4,264,571
[45] Apr. 28, 1981

[54] RADIOIMMUNOASSAY OF THYMOSIN $\alpha_1$

[75] Inventors: Allan L. Goldstein, Washington, D.C.; John E. McClure, Fairfax County, Va.

[73] Assignee: George Washington University, Washington, D.C.

[21] Appl. No.: 4,971

[22] Filed: Jan. 22, 1979

[51] Int. Cl.³ .................. G01N 33/48; G01T 1/00; A61K 43/00; C07G 7/00
[52] U.S. Cl. .................. 424/1; 23/230 B; 424/12; 424/177; 260/112 R; 260/112 B
[58] Field of Search .................. 424/1, 177, 12; 260/112, 15 R, 15 B; 23/230 B

[56] References Cited
U.S. PATENT DOCUMENTS

| | | | |
|---|---|---|---|
| 4,002,740 | 1/1977 | Goldstein et al. | 424/177 |
| 4,010,148 | 3/1977 | Goldstein et al. | 260/112.5 R |
| 4,082,737 | 4/1978 | McGregor et al. | 260/112.5 R |
| 4,148,788 | 4/1979 | Wang | 424/177 |

*Primary Examiner*—Benjamin R. Padgett
*Assistant Examiner*—Christine M. Nucker
*Attorney, Agent, or Firm*—Jon S. Saxe; Bernard S. Leon; George M. Gould

[57] ABSTRACT

An immunoassay for the polypeptidic thymic hormone thymosin $\alpha_1$ is described. Determination of thymosin $\alpha_1$ levels in biological fluids, particularly serum, provides a useful diagnostic test for immune deficiency diseases, autoimmune diseases, immunologically mediated diseases, neoplastic diseases and also allows one to monitor therapy with thymosin $\alpha_1$ by following blood levels of the hormone.

11 Claims, No Drawings

RADIOIMMUNOASSAY OF THYMOSIN $\alpha_1$

The invention described herein was made in part in the course of work under a grant or award from the Department of Health, Education and Welfare.

BACKGROUND OF THE INVENTION

Thymosin $\alpha_1$ is a heat stable, acidic polypeptide composed of 28 amino acid residues. This thymic hormone has been isolated from calf thymus thymosin fraction 5 and its amino acid sequence determined. Thymosin $\alpha_1$ is one of several polypeptides present in thymosin fraction 5 which participate in the regulation, differentiation and function of thymic dependent lymphocytes (T-cells). The isolation, characterization and use of thymosin $\alpha_1$ is described in greater detail in U.S. Pat. No. 4,079,127.

An immunoassay for a polypeptide hormone of the thymus known as thymopoietin or thymin is disclosed in U.S. Pat. No. 4,055,633. In particular, this patent discloses a radioimmunoassay for thymopoietin utilizing an antibody elicited by an immunogen comprising purified thymopoietin covalently coupled to an immunogenic carrier material such as bovine gamma globulin using glutaraldehyde as the coupling agent. The labelled antigen used in the assay is preferably $^{125}$I thymopoietin.

It should be noted that thymopoietin is totally non-analogous to thymosin $\alpha_1$ in structure, amino acid composition and sequence, biological activity profile, physical properties and immunological properties.

A radioimmunoassay for a partially purified thymosin fraction, i.e. thymosin fraction 6, which is now known to contain a mixture of a number of polypeptides, is reported by Schulof et al., Fed. Proc. 32, 962 (1973). See also Goldstein et al. Fed. Proc. 33, 2053 (1974).

DESCRIPTION OF THE INVENTION

The present invention relates to an immunoassay for thymosin $\alpha_1$. This immunopotentiating polypeptidic hormone is a component of thymosin fraction 5 and also has been found to be present in the blood of mammalian subjects.

The immunogen utilized to prepare the antibody for the instant assay is readily obtained by covalently bonding thymosin $\alpha_1$ to a conventional immunological carrier material. The source of the thymosin $\alpha_1$ is not narrowly critical to the practice of the invention. Suitable thymosin $\alpha_1$ can be derived from fraction 5 obtained from various mammalian sources. Thus, for example, thymosin $\alpha_1$ obtained from human, bovine, sheep or porcine fraction 5 preparations can be employed. This is possible due to the homology of amino acid sequences of thymosin $\alpha_1$ derived from these various mammalian species.

Alternatively, thymosin $\alpha_1$ obtained by peptide synthesis procedures now known in the art can be employed. Thus, for example, the synthesis of thymosin $\alpha_1$ by both solid phase and solution phase procedures is described in detail in U.S. patent application Ser. No. 917,059, filed June 19, 1978, entitled Synthesis of Thymosin Alpha$_1$, inventor Su-Sun Wang.

As used herein the term "immunogenic carrier material" is meant to include those materials which have the property of independently eliciting an immunogenic response in a host animal and which can be covalently coupled to thymosin $\alpha_1$ either directly via the formation of peptide or ester bonds between free carboxyl, amino or hydroxyl groups in thymosin $\alpha_1$ and corresponding groups on the immunogenic carrier material or alternatively by bonding through a conventional bifunctional linking group.

The covalent coupling of thymosin $\alpha_1$ to the immunogenic carrier material can be carried out in a manner well known in the art. Thus, for example, for direct covalent coupling it is possible to utilize a carbodiimide, most preferably dicyclohexylcarbodiimide or 1-ethyl-3-(3-dimethylaminopropyl)carbodiimide as coupling agent. In such direct coupling it is desirable to utilize a slightly acidic reaction medium for this step, e.g., a medium having a pH in the range of from about 3 to 6.5, most preferably in the range of from about 4 to 6.5.

A suitable bifunctional linking group for effecting coupling is a $C_{2-7}$ dialkanal such as glutaraldehyde. Such coupling in this alternate embodiment can conveniently be carried out using the conditions described by S. Avrameas, Immunochemistry 6, 43 (1969).

The resulting immunogen can be utilized without further purification or, although not necessary, after dialysis to remove any unreacted thymosin $\alpha_1$ and coupling reagents.

Suitable carrier materials which can be used in the preparation of the immunogens of the instant invention include proteins; natural or synthetic polymeric compounds such as polypeptides, e.g., polylysine or copolymers of amino acids; polysaccharides; and the like. Particularly preferred carrier materials are proteins and polypeptides, especially proteins.

The identity of the protein utilized in the preparation of an immunogen of the instant invention is not critical. Examples of suitable proteins include mammalian serum proteins such as, for example, human gamma globulin, human serum albumin, bovine serum albumin, methylated bovine serum albumin, rabbit serum albumin, bovine gamma globulin and equine gamma globulin or non-mammalian proteins such as hemocyanin. Other suitable proteins will be suggested to one skilled in the art.

The immunogen of the present invention may be utilized to induce formation of antibodies specific to thymosin $\alpha_1$ in host animals by injecting the immunogen in such a host, preferably using an adjuvant. Improved titers can be obtained by repeated injections over a period of time. Suitable host animals for this purpose include mammals such as rabbits, horses, goats, guinea pigs, rats, cows, sheep, etc. The resulting antisera will contain antibodies which will selectively complex with thymosin $\alpha_1$. Due to a high level of homology between the thymosin $\alpha_1$ sequences derived from various mammalian species, it is possible to utilize antibodies raised against one species of thymosin $\alpha_1$ to assay for thymosin $\alpha_1$ of other mammalian species.

Suitable labeled thymosin $\alpha_1$ for use in the immunoassay include radioisotopically labelled thymosin $\alpha_1$, particularly tritium ($^3$H), carbon 14 ($^{14}$C) or iodine 125 ($^{125}$I).

Tritium can be introduced into thymosin $\alpha_1$ by use of isotopic exchange procedures known in the art. The production of $^{14}$C-thymosin $\alpha_1$ is readily possible by incorporating one or more commercially available $^{14}$C-labelled amino acids into the appropriate steps of the thymosin $\alpha_1$ synthesis procedures referenced above.

A most preferred radiolabelled thymosin $\alpha_1$ is $^{125}$I-thymosin $\alpha_1$. The absence of tyrosine or histidine residues precludes the use of the direct radioiodination method involving Na $^{125}$I and chloramine-T. It is possible, however, to successfully introduce the $^{125}I$ label by using the Bolton-Hunter reagent ($^{125}I$-iodinated p-hydroxyphenylpropionic acid N-hydroxysuccinimide ester) as described in Biochem. J. 133, 529 (1973).

It is also within the scope of the invention to employ thymosin $\alpha_1$ labelled with any other unique and detectable lable such as for example chromophores, fluorophors, enzymes, red blood cells, latex particles or electron spin resonance groups.

Various assay methods can be employed in the practice of this invention. In one such procedure, known amounts of a sample to be assayed, the thymosin $\alpha_1$ specific antibody and the labelled thymosin $\alpha_1$ are mixed together and allowed to stand. The antibody-antigen complex is separated from the unbound reagents by procedures known in the art i.e., by treatment with ammonium sulphate, polyethylene glycol, second antibody either in excess or bound to an insoluble support, dextran coated charcoal and the like. The concentration of labelled thymosin $\alpha_1$ is determined in either the bound or unbound phase and the thymosin $\alpha_1$ content of the sample can then be determined by comparing the level of labelled component observed to a standard curve in a manner known per se. A suitable standard curve can be obtained by mixing known amounts of thymosin $\alpha_1$ with fixed amounts of labelled thymosin $\alpha_1$ and the thymosin $\alpha_1$ specific antibody and determining the degree of binding for each such known amount.

The present invention is further illustrated by the following examples.

EXAMPLE 1

Generation of Antisera

A. Coupling of synthetic thymosin $\alpha_1$ to hemocyanin by means of a glutaraldehyde Equivalent amounts (dry weight) of each protein, thymosin $\alpha_1$ and hemocyanin, were dissolved in 0.25 M $NaPO_4$, pH 7.0 buffer at a concentration of 2 mg/ml. Equal volumes of the protein solutions were mixed, and a volume of glutaraldehyde (25% aqueous solution) equal to 1% of the volume of the protein mixture was added. The reaction was allowed to continue for 3 hours while being stirred at room temperature. The reaction mixture was diluted in sterile saline to a final concentration of thymosin $\alpha_1$ of 100 ug/ml. The solution of coupled thymosin $\alpha_1$ was aliquoted and stored at 20° C.

B. Immunization and boosting protocol

The saline solution of thymosin $\alpha_1$ conjugate was emulsified with an equal volume of Freund's Complete Adjuvant to which had been added an additional amount of heat-killed *M. tuberculosis* bacilli. Each NZW rabbit (young 4–5 lb. animals of either sex) received 100 ug thymosin $\alpha_1$ and 8 mg *M. tuberculosis* H37RA bacilli in 2 ml of emulsion. Immunization was performed by injecting the emulsion into multiple intradermal sites (20–30 sites for each animal) on the backs of each rabbit. Each animal received four booster series of injections, again at multiple intradermal sites, with 50 ug thymosin $\alpha_1$ being given to each rabbit at weekly intervals. The first bleeding, one week after the series of boosts, demonstrated positive but low titers to thymosin $\alpha_1$. A rest period of 70 days was allowed before the next boost of 50 μg for each rabbit. A bleeding 10 days later proved to have an anti-thymosin $\alpha_1$ titer that was satisfactory for the RIA.

Bleeding of the rabbits was performed by venipuncture of the mid-ear artery. Blood was allowed to clot for 45 minutes at room temperature and to stand at 4° C. overnight before centrifugation. The serum was collected and stored at −20° C. in the presence of 0.05% sodium azide.

C. Titration of the antisera

Antisera in serial dilution were incubated with radiolabelled thymosin $\alpha_1$ and precipitated by the double antibody method. Upon measuring the percent cpm bound in the precipitate, a working final dilution of the antiserum which demonstrated 25–30% binding could be established. Antisera of equivalent titer were pooled and stored in small aliquots at −20° C.

EXAMPLE 2

Preparation of the Radiolabelled Thymosin $\alpha_1$

Synthetic thymosin $\alpha_1$, has been shown by several electrophoretic and chromatographic techniques to be identical to the natural peptide and to be of high purity. The method of Bolton and Hunter, supra was used for the introduction of an iodinated tyrosine moiety into the peptide. Thymosin $\alpha_1$ (5 ug), dissolved in 0.1 M sodium borate, pH 8.5 at a concentration of 0.5 mg/ml, was added to 1 mCi of dried Bolton-Hunter Reagent (New England Nuclear Product No. NEX-120H) in a Combi-V-vial cooled to near 0° C. on an ice bath. The reaction mixture was stirred by magnetic stirring bar for 40 minutes and was then diluted by the addition of 0.5 ml of 0.2 M glycine. Separation of iodinated peptide from the non-incorporated Bolton-Hunter Reagent was effected by gel filtration on a column of Sephadex G-10 equilibrated with a buffer consisting of phosphate-buffered saline and 0.1% gelatin, pH 7.4. Individual tubes of the void volume protein peak did not have differing immunoreactivities and were therefore pooled. Bolton-Hunter-labelled thymosin $\alpha_1$, having a specific radioactivity of approximately 3 uCi/ug was only 20% precipitable by 30% trichloroacetic acid but 94% precipitable by excess antiserum. The radiolabel from the Sephadex G-10 column separation was stored at constant −30° C. in small aliquots. The tracer was thawed as needed for assays and diluted with RIA buffer in order that 6000–7000 cpm were delivered to each assay tube in a volume of 50 ul. The tracer was sufficiently stable for use over a period of six weeks, although adjustment of the final working dilution of antiserum was required to keep binding of tracer at a level between 25–30% of total cpm available.

EXAMPLE 3

Radioimmunoassay Protocol

A standard stock solution of synthetic thymosin $\alpha_1$ was prepared consisting of the peptide at a concentration of 1 ug/ml in sterile 0.15 M sodium chloride. The stock solution, aliquoted in 1-ml volumes into plastic, capped tubes, was stored at constant 30° C. and thawed only once for use in preparing a standard curve. The stock solution was serially diluted in 0.4 ml RIA buffer in 12×75 mm glass disposable assay tubes. The standard curve consisted of duplicate sets of the stock solution serially diluted into twelve tubes each.

Unknown serum samples (0.2 ml serum) were pipetted into assay tubes containing 0.2 ml RIA buffer. Stock dilution of antiserum (50 ul volumes) was added to all tubes except control, non-specific binding (NSB) assay tubes. After rapid mixing of the solutions, the racks of assay tubes were incubated at 37° C. for 1 hour. Labelled trace, 6000–7000 cpm in 50 ul, was added. The contents of the tubes were mixed again, and the racks were incubated at 37° C. for 1 hour. The racks were transferred to a cold room (4° C.) for 48 hours.

Precipitation of the immune complexes was carried out by the double antibody method. Carrier normal rabbit globulin and goat anti-rabbit gamma globulins were first prepared by subjecting normal rabbit serum and the goat anti-rabbit globulin serum to fractionation with ammonium sulfate in order to remove low-molecular-weight serum components and to enrich for gamma globulins. The sera were treated with ammonium sulfate to a concentration of 30% of saturation at 4° C. The precipitated proteins were collected by centrifugation and redissolved in a volume of sterile 0.15 M sodium chloride equal to the original volume of serum. The volumes of each reagent for optimum precipitation of radiolabelled immune complexes were pre-determined in a titration experiment. Every new lot of normal rabbit IgG and goat anti-rabbit IgG must be standardized prior to their use in the radioimmunoassay.

After addition of normal rabbit globulin carrier and goat anti-rabbit gamma globulin reagents, the racks were incubated first for 1 hour at 37° C. and then for 16 hours at 4° C. Separation of the precipitated proteins from the radioactive supernatant was performed by centrifugation of the assay tubes at 2500 rpm for 20 minutes at 4° C. The supernatants were removed by aspiration, and the precipitates were washed by resuspension of 1 ml RIA buffer and one additional centrifugation. Assay tubes were finally tranferred to an automated gamma spectrometer for estimation of the amount of radioactivity bound in the protein pellets.

Serum samples (0.2 ml) were assayed in triplicate tubes. The average cpm for the NSB (control) was subtracted from each sample value. The values of cpm bound for each standard and sample tube were subjected to computation on a programmable Wang 720C desk top calculator. For the standard curve, the cpm bound in the presence of a known amount of thymosin $\alpha_1$ divided by the cpm bound in the absence of thymosin $\alpha_1$ was calculated (Bi/Bo). A transformation known as a logit (Y) was calculated as well as the $\log_{10}$ of the amount of standard thymosin $\alpha_1$ in femtomoles (X).

$$\text{Logit } (B_i/B_o) = \ln \frac{B_i/B_o}{(1 - B_i B_o)} = Y$$

The method of least squares was used to calculate the best straight line from the values of X and Y; the slope, Y-intercept, and the correlation coefficient were programmed for the output. The amount of thymosin $\alpha_1$ cross-reacting material in the serum samples was calculated from the values of Logit ($B_i/B_o$) for each unknown and from the slope and Y-intercept of the standard curve. The values of femtomoles of thymosin $\alpha_1$ from triplicate analyses were subjected to further analysis in order to determine mean values, standard error, and percent standard error. Serum levels for normal and immunodeficient patients have been reported in terms of femtomoles/0.2 ml serum.

EXAMPLE 4

Experimental Results

The radioimmunoassay procedure of Example 3 was run on serum samples from several strains of mouse and from one strain of guinea pig. The sensitivity of the assay was sufficient to detect cross-reacting material in such serum using the human thymosin $\alpha_1$ reagents. Resulting data is summarized in Table 1 below:

TABLE 1

Serum Levels of Thymosin-$\alpha_1$ in Experimental Animal Models

| Species/Strain | Serum Concentration of Thymosin-$\alpha_1$ (pmoles/ml ± S.E.) |
|---|---|
| Mouse - Balb/c (Normal adult) | 10.6 ± 2.1 |
| Mouse - NZB* (Adult) | Not detectable |
| Mouse - B/W* (Adult) | 2.66 ± 1.5 |
| Guinea Pig - Hartley (Adult) | 8.15 ± 3.5 |

*Mice which exhibit manifestations of autoimmune disease

It is seen from Table 1 that the serum levels of thymosin $\alpha_1$ in normal Balb/c mice are apparently quite different from NZB and B/W mice (strains of mice which express autoimmune-like symptoms.

Frozen serum samples obtained from normal male human subjects of varying ages was also assayed by the procedure of Example 3 and the results are summarized in Table 2:

TABLE 2

Thymosin $\alpha_1$ Levels in Frozen Sera of Normal Human Males

| Age Group (years) | No. of Patients in Study | Concentration of Thymosin-$\alpha_1$ (pmoles/ml ± S.E.) |
|---|---|---|
| 10–19 | 5 | 1.82 ± 0.20 |
| 20–29 | 4 | 1.90 ± 0.57 |
| 30–39 | 7 | 1.07 ± 0.20 |
| 40–49 | 6 | 1.19 ± 0.26 |
| 50–59 | 6 | 0.66 ± 0.06 |

These very preliminary data seem to suggest a decline in thymosin $\alpha_1$ serum levels with age. It should be noted that the length of time serum samples have been stored frozen may affect the estimates of thymosin $\alpha_1$ concentration. The serum samples of normal males had been frozen for as long as three years. Values for these frozen samples appear to be significantly lower than values obtained for fresh, non-frozen serum from adult males. However, the comparative levels vs age would not be affected by the period of storage.

We claim:

1. An immunogen consisting essentially of thymosin $\alpha_1$ covalently bonded to an immunogenic carrier material.

2. The immunogen of claim 1 wherein said immunogenic carrier material is a protein.

3. The immunogen of claim 2 wherein said protein is hemocyanin.

4. The immunogen of claim 3 wherein said thymosin $\alpha_1$ is covalently bonded to said immunogenic carrier material through a $C_{2-7}$ dialkanal bifunctional linking group.

5. The immunogen of claim 4 wherein said linking group is glutaraldehyde.

6. An antibody specific to thymosin $\alpha_1$, said thymosin $\alpha_1$ specific antibody being prepared by innoculating a host animal with the immunogen of claim 1 and collecting the serum from said host animal.

7. $^{125}$I-thymosin $\alpha_1$.

8. A method for the assay of thymosin $\alpha_1$ in a sample, which method comprises mixing said sample with a known amount of labelled thymosin $\alpha_1$ and an antibody which will selectively complex with said thymosin $\alpha_1$, separating the resulting antibody-antigen complex from uncomplexed labelled thymosin $\alpha_1$, measuring the degree of binding of the said labelled thymosin $\alpha_1$ in said complex and determining the amount of thymosin $\alpha_1$ present in said sample by comparing said degree of binding to a standard curve obtained by mixing known amounts of thymosin $\alpha_1$ with fixed amounts of said labelled thymosin $\alpha_1$, and said antibody and determining the degree of binding for each known amount of thymosin $\alpha_1$.

9. The method of claim 8 wherein a radioimmunoassay is employed and radiolabelled thymosin $\alpha_1$ is used.

10. The method of claim 9 wherein said radiolabelled thymosin $\alpha_1$ is $^{125}$I-thymosin $\alpha_1$.

11. The method of claim 8 wherein the antibody-antigen complex is separated from solution with the assistance of a double antibody technique using a second antibody immunologically reactive against the serum of the hose animal in which the thymosin $\alpha_1$ specific antibody was elicited.

* * * * *